(12) United States Patent
Pease et al.

(10) Patent No.: US 11,034,721 B2
(45) Date of Patent: Jun. 15, 2021

(54) METHOD FOR THE REDUCTION OF VIRAL TITER IN PHARMACEUTICALS

(71) Applicant: LONZA LTD, Visp (CH)

(72) Inventors: Paul Pease, Durham, NH (US);
Wilburn Miller, Portsmouth, NH (US);
Jesse Cobb, Portsmouth, NH (US);
Anthony Castagnaro, Alton Bay, NH (US); Andrew Harris, Raymond, NH (US)

(73) Assignee: LONZA LTD, Visp (CH)

( * ) Notice: Subject to any disclaimer, the term of this patent is extended or adjusted under 35 U.S.C. 154(b) by 291 days.

(21) Appl. No.: 15/836,683

(22) Filed: Dec. 8, 2017

(65) Prior Publication Data
US 2018/0162903 A1 Jun. 14, 2018

Related U.S. Application Data

(60) Provisional application No. 62/432,273, filed on Dec. 9, 2016.

(51) Int. Cl.
*B01D 61/12* (2006.01)
*G01N 30/28* (2006.01)
(Continued)

(52) U.S. Cl.
CPC .............. *C07K 1/34* (2013.01); *B01D 61/00* (2013.01); *B01D 61/14* (2013.01); *B01D 61/22* (2013.01);
(Continued)

(58) Field of Classification Search
CPC ... C12N 7/00; C12N 7/01; C12N 7/02; C12N 7/04; C12N 7/08; C12M 1/00;
(Continued)

(56) References Cited

U.S. PATENT DOCUMENTS 5,656,491 A    8/1997  Cassani et al.
6,365,395 B1 * 4/2002  Antoniou ............ B01D 61/142
                                              210/767

(Continued)

FOREIGN PATENT DOCUMENTS

EP    2725033 A1    4/2014

OTHER PUBLICATIONS

LCGC Europe, Jul. 2014, vol. 27, No. 7 (Year: 2014).*
(Continued)

*Primary Examiner* — Allison G Fitzsimmons
(74) *Attorney, Agent, or Firm* — Dority & Manning, P.A.

(57) ABSTRACT

Disclosed are methods and devices for the optimization of virus removal from solutions. A method of filtering a process fluid comprising a product includes allowing some of the process fluid to flow from a first reservoir to a viral filter; adding a chase fluid to the process fluid in the first reservoir to form a composite fluid; and allowing the composite fluid to flow from the first reservoir to the viral filter to produce eluent. In some embodiments, flow of fluid across the viral filter is sufficient to avoid significant impairment to viral removal until a preselected event, occurs. In some embodiments, flow of fluid from the first reservoir across the viral filter is maintained in the absence of an interruption or slowing of flow of duration or magnitude sufficient to impair viral removal to a level below a log-reduction value of the viral filter.

27 Claims, 1 Drawing Sheet

(51) Int. Cl.
  *C07K 1/34* (2006.01)
  *C07K 16/06* (2006.01)
  *B01D 61/00* (2006.01)
  *B01D 63/02* (2006.01)
  *C07K 16/08* (2006.01)
  *B01D 61/14* (2006.01)
  *B01D 61/22* (2006.01)
  *C07K 1/36* (2006.01)

(52) U.S. Cl.
  CPC ............ *B01D 63/02* (2013.01); *C07K 16/065* (2013.01); *C07K 16/08* (2013.01); *G01N 30/28* (2013.01); *C07K 1/36* (2013.01)

(58) Field of Classification Search
  CPC .......... C12M 1/12; B01D 61/00; B01D 61/14; B01D 61/142; B01D 61/145; B01D 61/147; B01D 61/16; B01D 61/18; B01D 61/22; B01D 61/58; B01D 2311/00; B01D 2311/02; B01D 2311/04; B01D 2311/14; B01D 2311/16; B01D 2311/22; B01D 2311/26; B01D 2311/2649; B01D 63/02; G06F 3/0482; G06F 3/048; G06F 3/0481; G06F 3/04842; G06F 3/04847; G06F 3/0486; G06F 3/1454; G06F 3/16; G09B 5/00; G09B 7/02; G09B 5/06; G09B 5/065; G09B 7/06; C07K 16/065; C07K 16/08; C07K 1/34; C07K 1/36; G01N 30/28; G06Q 10/06311; G06Q 10/101; G06Q 30/0282; G06Q 50/20; G06T 11/60; G09G 2354/00; G09G 2370/022; G09G 5/12; G11B 27/105; G11B 27/34

USPC ............ 435/239, 237, 238, 308.1; 530/427; 210/661, 660, 767, 255, 262
  See application file for complete search history.

(56) References Cited

U.S. PATENT DOCUMENTS

| | | |
  |---|---|---|
  | 7,629,167 B2 | 12/2009 | Hodge et al. |
  | 8,298,054 B2 | 10/2012 | Hodge et al. |
  | 2009/0305626 A1 | 12/2009 | Hope |
  | 2010/0170852 A1* | 7/2010 | Suh .................. B01J 20/287 210/656 |
  | 2012/0077429 A1 | 3/2012 | Wernimont et al. |
  | 2013/0280797 A1 | 10/2013 | Rao et al. |
  | 2013/0345402 A1 | 12/2013 | Vogel et al. |
  | 2014/0309408 A1* | 10/2014 | Demina .................. C12N 7/00 530/413 |
  | 2015/0111252 A1* | 4/2015 | Hirschel ................ C12M 41/48 435/70.3 |
  | 2015/0183815 A1 | 7/2015 | Kopf et al. |

OTHER PUBLICATIONS

Pesticide Analytical Manual vol. I, Chapter 6 (Year: 1999).*
  Sigma-Aldrich, Bulletin 826E, HPLC Troubleshooting Guide, St. Louis MO (Year: 2009).*
  International Search Report and Written Opinion for International Application No. PCT/US2017/065424 dated Apr. 4, 2018.

* cited by examiner

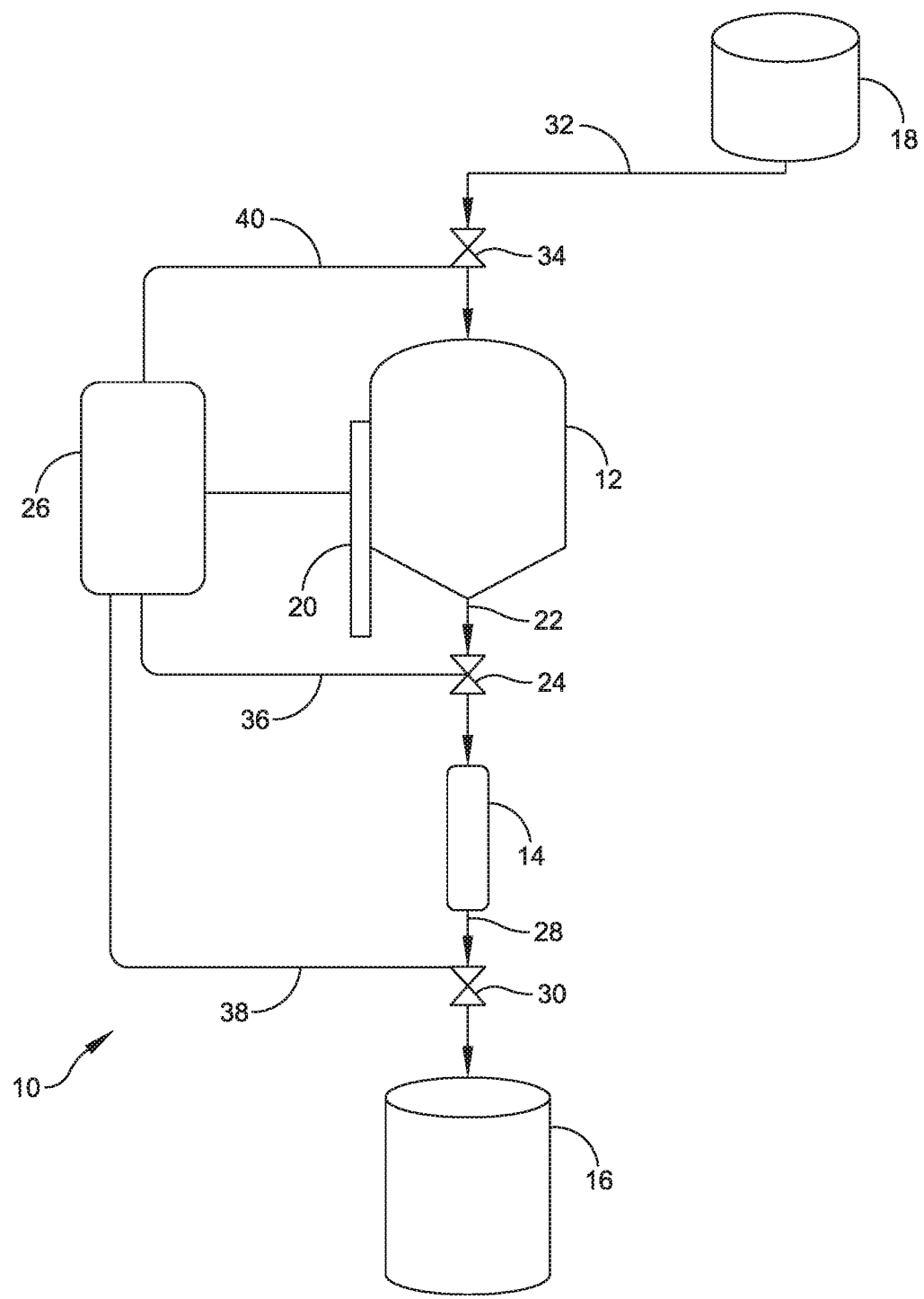

METHOD FOR THE REDUCTION OF VIRAL TITER IN PHARMACEUTICALS

CROSS REFERENCE TO RELATED APPLICATIONS

This application claims the benefit of priority to U.S. Provisional Patent Application Ser. No. 62/432,273 filed on Dec. 9, 2016, which is hereby incorporated herein by reference in its entirety for all purposes.

FIELD OF THE INVENTION

The invention relates to methods and devices for the optimization of virus removal from solutions, e.g., cell culture fluids.

BACKGROUND

Products of cell culture, including recombinant therapeutic proteins, are used in many applications, including the treatment of a wide diversity of medical conditions, ranging from metabolic disorders to cancer. These proteins can be synthesized by large-scale cultivation of cells, e.g., genetically engineered cells that contain heterologous nucleic acids encoding the proteins. These protein products must meet rigorous regulatory and quality standards for use in therapies in human patients. The minimization of viral contamination of such products is an important aspect of product safety and quality. There exists a need for more efficient systems, processes, and methods for the commercial manufacture of recombinant protein therapeutics that meet Good Manufacturing Practices (GMP) standards at an acceptable cost, quality, and at the desired quantities.

SUMMARY

An important aspect of the production of products, e.g. protein products, e.g., recombinant protein therapeutics, is the removal of virus or viral particles after production or fermentation. Methods described herein optimize the inactivation or removal of viruses from product preparations, e.g., from a feed from a bioreactor While not wishing to be bound by theory, it is believed that interruptions in the flow of product-containing fluid across a viral filter results in a preparation of lesser purity and that by maintaining flow the purity or reduction of viral contamination can be optimized.

According to an aspect of the present disclosure, a method of filtering a process fluid comprising a product, the method comprises a) allowing some of the process fluid in a first reservoir to flow out of the first reservoir and pass a viral filter to produce eluent; b) adding a chase fluid to the process fluid in the first reservoir to form a composite fluid; and c) allowing the composite fluid, in the first reservoir to flow out of the first reservoir and pass the viral filter to produce eluent, wherein flow of fluid across the viral filter is sufficient to avoid significant impairment to viral removal, until a preselected event, occurs, and wherein flow of fluid from the first reservoir across the viral filter is maintained in the absence of an interruption or slowing of flow of duration or magnitude sufficient to impair viral removal to a level below a log-reduction value of the viral filter.

In some embodiments, the product includes an active pharmaceutical ingredient.

In some embodiments, allowing some of the process fluid in the first reservoir to flow out of the first reservoir and through the viral filter reduces an amount of process fluid remaining in the first reservoir.

In some embodiments, adding the chase fluid is performed prior to emptying of the first reservoir of process fluid.

In some embodiments, adding the chase fluid is performed when the volume of process fluid remaining in the first reservoir is at a reference volume or within a reference volume range.

In some embodiments, the reference volume is equal to or greater than 0.5, 1, 1.5, 2, 3, 5 or 10, times a volume of components disposed between the first reservoir and a destination reservoir.

In some embodiments, the reference volume is equal to or greater than a volume of components disposed between the first reservoir and a destination reservoir.

In some embodiments, the volume of chase fluid added is less than or equal to a chase fluid reference volume.

In some embodiments, the chase fluid reference volume is equal to or greater than 0.5, 1, 1.5, 2, 3, 5 or 10, times a volume of components disposed between the first reservoir and a destination reservoir.

In some embodiments, the chase fluid reference volume is equal to or greater than a volume of components disposed between the first reservoir and the destination reservoir.

In some embodiments, the chase fluid is added to the first reservoir while the first reservoir still contains a predetermined amount of process fluid.

In some embodiments, the method further comprises determining a value that is a function of the amount of process fluid remaining in the first reservoir.

In some embodiments, the method further comprises determining whether the value meets a predetermined reference value.

In some embodiments, the method further comprises, if the value has a predetermined relationship with the reference value, adding chase fluid to the first reservoir.

In some embodiments, a ratio of an amount of chase fluid to an amount of process fluid remaining in the first reservoir when the chase fluid is added is equal to or greater than 1:0.05, 1:1, 1.5:1, 2:1, 3:1, 5:1, or 10:1.

In some embodiments, flow of fluid from the first reservoir across the viral filter is maintained at a preselected rate.

In some embodiments, a preselected difference in pressure across the viral filter, is maintained.

In some embodiments, a differential pressure across the viral filter is maintained at or below a preselected maximal value.

In some embodiments, a preselected difference in pressure, equal to or no greater than 14 psi, 11 psi, or 13.2 psi of differential pressure across the viral filter is maintained.

In some embodiments, a differential pressure across the viral filter is maintained at or above a preselected minimal value.

In some embodiments, a differential pressure across the viral filter sufficient that a reduction in viral particles of at least 5, 10, 15, 20, 30, 40, 50, 60, 70, 80, 90, or 100 fold is achieved.

In some embodiments, any single stoppage of the flow of fluid from the first reservoir is less than 1, 10, or 60 minutes in duration.

In some embodiments, there is continuous flow during one, two or all of steps a, b, and c.

In some embodiments, the preselected event includes eliminating a fluid connection between the viral filter and a destination reservoir.

In some embodiments, the preselected event includes sending the eluent to a subsequent operation.

In some embodiments, the preselected event includes stopping the flow from the viral filter into the accumulated eluent.

In some embodiments, the preselected event includes stopping the flow from the viral filter into a destination reservoir.

In some embodiments, the preselected event includes collecting eluent produced from the flow of fluid from the first reservoir.

In some embodiments, the preselected event includes reaching the end of a preselected time period.

In some embodiments, the method further comprises providing a system including the first reservoir, the viral filter, and a destination reservoir, wherein the first reservoir is in fluid connection with the viral filter and, the viral filter is in fluid connection with the destination reservoir.

In some embodiments, the viral filter is disposed between the first reservoir and the destination reservoir.

In some embodiments, the viral filter is disposed between the first reservoir and a conduit.

In some embodiments, the system includes a pre-filter conduit configured to convey fluid from the first reservoir to the viral filter.

In some embodiments, the system includes a conduit configured to convey fluid to the destination reservoir or a conduit to a destination.

In some embodiments, the system includes a first conduit configured to convey fluid from the first reservoir to the viral filter, and a second conduit configured to convey fluid from the viral filter to the destination reservoir.

In some embodiments, the system includes a first valve disposed to control the flow of fluid from the first reservoir to the viral filter.

In some embodiments, the system includes a second valve disposed to control the flow of fluid from the viral filter to the destination reservoir.

In some embodiments, the system includes a computer or microprocessor for controlling one or more valves.

In some embodiments, the viral filter is integral with a wall of the first or second reservoir.

In some embodiments, flow of fluid from the first reservoir across the viral filter is maintained in the absence of a stoppage of the flow.

According to another aspect of the present disclosure, a method of filtering a process fluid comprising a product, comprises a) allowing process fluid in a first reservoir to flow out of the first reservoir and pass a viral filter to produce eluent and to reduce an amount of process fluid in the first reservoir; b) determining a value which is a function of the amount of process fluid remaining in the first reservoir and, if the value meets a predetermined reference value, adding chase fluid, to the process fluid in the first reservoir to form a composite fluid, wherein the chase fluid is added to the first reservoir while the first reservoir still contains a predetermined amount of process fluid; c) allowing the composite fluid in the first reservoir to flow out of the first reservoir and pass the viral filter to produce eluent; and d) stopping the flow from the viral filter, wherein flow of fluid from the first reservoir across the viral filter is sufficient to avoid significant impairment to viral removal until stopping the flow from the viral filter.

In one aspect, the disclosure provides a method of filtering a process fluid comprising a product. The method comprises allowing process fluid in a first (or sending) reservoir to flow out of the first reservoir and pass a viral filter to produce eluent. Chase fluid is added to the process fluid in the first reservoir to form a composite fluid. The method further comprises allowing the composite fluid in the first reservoir to flow out of the first reservoir and pass the viral filter to produce eluent. Flow of first reservoir fluid across the viral filter is sufficient to avoid significant impairment to viral removal until a preselected event, e.g., the collection of accumulated eluent occurs.

In an embodiment, the product comprises an active pharmaceutical ingredient (API).

In an embodiment, allowing process fluid in the first reservoir to flow out of the first reservoir and through the filter reduces the amount of process fluid remaining in the first reservoir.

In an embodiment, chase fluid is added to process fluid prior to emptying of the first reservoir of process fluid.

In an embodiment, chase fluid is added when the volume of process fluid remaining in the first reservoir is at or within a reference volume.

In an embodiment, the reference volume is equal to or greater than 0.5, 1, 1.5, 2, 3, 5 or 10, times the volume of the components disposed between the first reservoir and a destination reservoir, e.g., piping and filter.

In an embodiment, the reference volume is equal to or greater than the volume of the components, e.g., piping and filter, disposed between the first reservoir and a destination reservoir.

In an embodiment, the volume of chase fluid added is at or within a reference volume.

In an embodiment, the reference volume is equal to or greater than 0.5, 1, 1.5, 2, 3, 5 or 10, times the volume of the components disposed between the first reservoir and a destination reservoir, e.g., piping and filter.

In an embodiment, the reference volume is equal to or greater than the volume of the components, e.g., piping and filter, disposed between the first reservoir and a destination reservoir.

In an embodiment, the chase fluid is added to the first reservoir while the first reservoir still contains a predetermined amount of process fluid, e.g., at least 1, 2, 3, 4, 5, 10, 20, 30, 40, or 50% of the original amount of process fluid.

In an embodiment, the method comprises determining a value that is a function of the amount of process fluid remaining in the first reservoir.

In an embodiment, the method comprises determining if the value meets a predetermined reference value.

In an embodiment, if the value has a predetermined relationship with the reference value (e.g., if it meets, or exceeds, or is less than the reference value) chase fluid is added to the first reservoir.

In an embodiment, the ratio of the amount of chase fluid to the amount of process fluid remaining in the first reservoir when the chase fluid added is equal to or greater than 1:0.05, 1:1, 1.5:1, 2:1, 3:1, 5:1, or 10:1.

In an embodiment, flow of a first reservoir fluid across the viral filter is maintained in the absence of an interruption or slowing of flow of sufficient duration or magnitude that a significant impairment to viral removal.

In an embodiment, the flow is of sufficient duration or magnitude that a reduction in viral particles of at least 5, 10, 15, 20, 30, 40, 50, 60, 70, 80, 90, or 100 fold is achieved.

In an embodiment, flow of first reservoir fluid across the viral filter is maintained at a preselected rate.

In an embodiment, a preselected difference in pressure, e.g., a preselected range of differential pressure across the viral filter is maintained.

In an embodiment, a differential pressure across the viral filter is maintained at or below a preselected maximal value.

In an embodiment, a preselected difference in pressure, equal to or no greater than 14 psi, 11 psi, or 13.2 psi of differential pressure across the filter is maintained.

In an embodiment, a differential pressure across the viral filter is maintained at or above a preselected minimal value.

In an embodiment, a differential pressure across the viral filter sufficient that a reduction in viral particles of at least 5, 10, 15, 20, 30, 40, 50, 60, 70, 80, 90, or 100 fold is achieved.

In an embodiment, the flow of first reservoir fluid is stopped for a total of less than 1, 10, 60, 120, or 180 minutes.

In an embodiment, any single stoppage of the flow of first reservoir fluid is less than 1, 10, 60, 120, or 180 minutes in duration.

In an embodiment, there is continuous flow during one, two or all of the steps of a) allowing process fluid in a first (or sending) reservoir to flow out of the first reservoir and pass a viral filter to produce eluent; b) adding chase fluid, to the process fluid, in the first reservoir to form a composite fluid; and/or c) allowing the composite fluid, in the first reservoir to flow out of the first reservoir and pass the viral filter to produce eluent.

In an embodiment, the preselected event comprises eliminating a fluid connection between the viral filter and a second or destination reservoir.

In an embodiment, the preselected event comprises sending the eluent to the next unit operation.

In an embodiment, the preselected event comprises stopping the flow from the viral filter into the accumulated eluent.

In an embodiment, the preselected event comprises stopping the flow from the viral filter into the second or destination reservoir.

In an embodiment, the preselected event comprises collecting eluent produced from the flow of first reservoir fluid.

In an embodiment, the preselected event comprises reaching the end of a preselected time period.

In an embodiment, the method comprises providing a system comprising: a first (or sending) reservoir; a viral filter, and (optionally) a second reservoir, e.g., a receiving tank, wherein the first reservoir is in fluid connection with the viral filter and, (optionally) the filter is in fluid connection with a second reservoir.

In an embodiment, the viral filter is disposed between the first reservoir and a second or destination reservoir.

In an embodiment, the viral filter is disposed between the first reservoir and a conduit, e.g., a pipe, to a destination, e.g., the next unit operation.

In an embodiment, the system comprises a conduit configured to convey fluid from the first reservoir to the viral filter.

In an embodiment, the system comprises a conduit configured to convey fluid, e.g., eluent, from the viral filter to a second or receiving reservoir or a conduit, e.g., a pipe, to a destination, e.g., the next unit operation.

In an embodiment, the system comprises a conduit configured to convey fluid from the first reservoir to the viral filter; and a conduit configured to convey fluid, e.g., eluent, from the viral filter to a second reservoir.

In an embodiment, the system comprises a valve disposed to control the flow of fluid from the first reservoir to the viral filter.

In an embodiment, the system comprises a valve disposed to control the flow of fluid, e.g., eluent, from the viral filter to the second reservoir.

In an embodiment, the system comprises a computer or microprocessor to control a valve.

In an embodiment, the filter is integral with the wall of the first or second reservoir.

In another aspect, the disclosure provides a method of filtering a process fluid comprising a product. The method includes allowing a process fluid in a first reservoir to flow out of the first reservoir and pass a viral filter to produce eluent and to reduce the amount of process fluid in the first reservoir and determining a value which is a function of the amount of process fluid remaining in the first reservoir and if the value meets a predetermined reference value, adding chase fluid, to the process fluid, in the first reservoir to form a composite fluid, wherein the chase fluid is added to the first reservoir while the first reservoir still contains a predetermined amount of process fluid. The composite fluid in the first reservoir is allowed to flow out of the first reservoir and pass the viral filter to produce eluent. The method further include stopping the flow from the viral filter into the accumulated eluent, wherein flow of first reservoir fluid across the viral filter is sufficient to avoid significant impairment to viral removal or removal, until stopping the flow from the viral filter into the accumulated eluent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

The drawing is first briefly described.

FIG. 1 is a diagram of a system for viral purification of a cell culture fluid.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

"Eluent", as that term is used herein, refers to fluid that has passed, e.g., flowed through, a viral filter. In embodiments, the amount or concentration of virus in eluent is less than in the culture fluid or composite fluid prior to passing the viral filter.

"First reservoir fluid" as that term is used herein refers collectively to one or more or all of culture fluid, chase fluid and composite fluid.

As used herein, the terms "peptide," "polypeptide," and "protein" are used interchangeably, and refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

"Product" as that term is used herein refers to a molecule, nucleic acid, polypeptide, or any hybrid thereof, that is produced, e.g., expressed, by a cell which has been modified or engineered to produce the product. In one embodiment, the product is a naturally occurring product or a non-naturally occurring product, e.g., a synthetic product. In one embodiment, a portion of the product is naturally occurring, while another portion of the product is non-naturally occurring. In one embodiment, the product is a polypeptide, e.g., a recombinant polypeptide. In one embodiment, the product is suitable for diagnostic or pre-clinical use. In another embodiment, the product is suitable for therapeutic use, e.g., for treatment of a disease. In one embodiment, the modified or engineered cells comprise an exogenous nucleic acid that controls expression or encodes the product. In other embodiments, the modified or engineered cells comprise other molecules, e.g., that are not nucleic acids, that controls the expression or construction of the product in the cell.

"Recombinant polypeptide" or "recombinant protein" as those terms are used herein refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering (of the cell or of a precursor cell). E.g., at least one nucleotide was altered, e.g., it was introduced into the cell or it is the product of a genetically engineered rearrangement. In an embodiment, the sequence of a recombinant polypeptide does not differ from a naturally occurring isoform of the polypeptide or protein. In an embodiment, the amino acid sequence of the recombinant polypeptide differs from the sequence of a naturally occurring isoform of the polypeptide or protein. In an embodiment, the recombinant polypeptide and the cell are from the same species. In an embodiment, the recombinant polypeptide is endogenous to the cell, in other words, the cell is from a first species and the recombinant polypeptide is native to that first species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from different species, e.g., the recombinant polypeptide is a human polypeptide and the cell is a non-human, e.g., a rodent, e.g., a CHO, or an insect cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally occurring isoform of the human polypeptide or protein. In an embodiment, the recombinant polypeptide differs from a naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide by no more than 1, 2, 3, 4, 5, 6, 7, 8, 9, 10, or 15% of its amino acid residues.

System for the Optimization of Viral Removal

According to one aspect of the present disclosure, a system for the optimization of viral removal comprises at least one product holding tank connected to at least one chase fluid reservoir at an inlet of the at least one product holding tank, at least one viral filter connected to an outlet of the at least one product holding tank, at least one eluent reservoir connected to the at least one viral filter. In some embodiments, a controller adjusts flow of a chase fluid from the at least one chase fluid reservoir into the at least one product holding tank. In some embodiments, the controller adjusts a first flow rate of the chase fluid from the at least one chase fluid reservoir to match a second flow rate, such as a flow rate of fluid from the at least one product holding tank or a flow rate through a viral filter downstream of the at least one product holding tank.

According to an aspect of the present disclosure, a system for filtering a process fluid comprising a product is provided. In some embodiments, the product comprises an active pharmaceutical ingredient. The system can be used with the any of the methods for filtering a process fluid according to the present disclosure. FIG. 1 shows an embodiment of a production system indicated generally at 10 including a product holding tank (a first reservoir) 12 that leads to a viral filter 14. In the embodiment of FIG. 1, the viral filter 14 leads to an eluent reservoir (second reservoir) 16. In some embodiments, the eluent reservoir 16 is not included. A chase fluid reservoir leads to the first reservoir 12.

The first reservoir 12 facilitates the proliferation and maintenance of cells or cell lines. For example, in some embodiments, the first reservoir 12 facilitates the proliferation and maintenance of cells or cell lines described herein.

The first reservoir 12 may include or be connected to a bioreactor and or a culture module. The bioreactor and/or the culture module may be rotated or agitated within the overall device via control actuators. Rotation of the first reservoir 12 about an axis may enable the beneficial use of gravity to effect specific bioprocessing sequences such as sedimentation-based cell seeding and fluid exchange within the bioreactor.

In embodiments, the bioreactor comprises a bioreactor housing having one or more inlet ports and one or more outlet ports for media flow and at least one chamber defined within said bioreactor housing for receiving cells and facilitating cell culture and protein production. The chamber may be selected from the group consisting of a cell culture/proliferation chamber and/or protein production chamber. Furthermore, the chamber houses one or more substrates and/or scaffolds. In embodiments of the invention, the bioreactor includes two chambers that are operably connected within the bioreactor. Alternatively, the two chambers may be independently operable or co-operatively operable. In still further aspects, the chambers and/or bioreactors are operably connected to provide for the exchange of fluids, cells and/or tissues between the chambers and/or bioreactors. The scaffold for use in the present invention is selected from the group consisting of a porous scaffold, a porous scaffold with gradient porosity, a porous reticulate scaffold, a fibrous scaffold, a membrane encircled scaffold and combinations thereof. Funnels or similar passageways may be provided between chambers within a bioreactor. Furthermore, one or more filters may be provided at any location within a bioreactor.

The cell culture device (or culture module) described herein in various embodiments is under the control of one or more microprocessors that may be preprogrammed in order that the user can select a specific type of environment (or sequence of environments) within the bioreactor such as cell proliferation, cell maintenance, protein production, or protein secretion. This eliminates operator intervention and reduces the possibility of inadvertent contamination.

Associated with the first reservoir 12 is a sensor assembly 20 that is configured to monitor the amount of fluid in the first reservoir 12. The sensor assembly 20 can also sense a rate of change of the amount of fluid in the first reservoir 12 in some embodiments. In some embodiments, the sensor assembly 20 is embedded in or secured to a wall of the first reservoir 12. In some embodiments, the sensor assembly 20 may include a mechanical sensor, an electrical sensor, an optical sensor, and/or another sensor.

The product holding tank (first reservoir) 12 is in fluid connection with the viral filter 14. In FIG. 1, the viral filter 14 is disposed between the first reservoir 12 and the second reservoir 16, so fluid flows from the first reservoir 12 to the viral filter 14, and then to the second reservoir 16. In particular, a pre-filter conduit (a first conduit) 22 is configured to convey fluid from the first reservoir 12 to the viral filter 14. In some embodiments, the pre-filter conduit 22 is a pipe.

The pre-filter conduit 22 may include a standard pipe used in biological processing operations. In some embodiments, the pre-filter conduit 22 has an outer diameter of 2 inches. In some embodiments, the pre-filter conduit 22 is sanitary piping. In some embodiments, the pre-filter conduit 22 is disposable tubing.

To control flow from the first reservoir 12 to the viral filter 14, a first valve 24 is disposed along the pre-filter conduit 22 between first reservoir 12 and the virus filter 14. The first valve 24 allows fluid communication between the first reservoir 12 and the virus filter 14. The first valve 24 is capable of being controlled by a processor 26 to adjust the flow of fluid from the first reservoir 12 to the viral filter 14. The first valve 24 may be opened to allow fluid to flow from the first reservoir 12 to the viral filter 14. In some embodiments, the first valve 24 may be adjusted between an open position and a closed position to throttle the flow of fluid from the first reservoir 12 to the viral filter 14.

Although the viral filter 14 in FIG. 1 is shown separate from the first reservoir 12 and the second reservoir 16, in some embodiments the viral filter 14 is integral with the wall of the first reservoir 12 or the second reservoir 16.

The viral filter 14 is disposed between the pre-filter conduit 22 and a post-filter conduit 28 that connects the viral filter 14 to the second reservoir 16 and that is configured to convey fluid, such as eluent, from the viral filter 14 to the second reservoir 16. In some embodiments, the post-filter conduit 28 is a pipe. The post-filter conduit 28 may include a standard pipe used in biological processing operations. In some embodiments, the post-filter conduit 28 has an outer diameter of 2 inches. In some embodiments, the post-filter conduit 28 is sanitary piping. The viral filter 14 is in fluid connection with the eluent reservoir (the second reservoir) 16 via the post-filter conduit 28.

The viral filter 14 has a certain validated capacity for viral removal, such as a log-reduction value. If the process fluid contains more material to be removed in excess of the validated capacity, a plurality of viral filters can be used in parallel.

A second valve 30 is disposed along the post-filter conduit 28 and is configured to regulate (stop or allow) fluid flow between viral filter and 14 and eluent reservoir 16. The second valve 30 is capable of being controlled by the processor 26 to adjust the flow of fluid, such as eluent, from the viral filter 14 to the second reservoir 16. The second valve 30 may be opened to allow fluid to flow from the viral filter 14 to the second reservoir 16. In some embodiments, the second valve 30 may be adjusted between an open position and a closed position to throttle the flow of fluid from the viral filter 14 to the second reservoir 16. In some embodiments, the second reservoir 16 is referred to as a destination reservoir.

When the system 10 is used for performing a subsequent biological processing operation that does not require the second reservoir 16, the post-filter conduit 28 may be connected to a destination or a destination reservoir other than the second reservoir 16. In various embodiments, the post-filter conduit 28 is configured to convey fluid, such as eluent, to the second reservoir 16, another destination, or another conduit to a destination.

A chase fluid reservoir 18 is connected to the first reservoir 12 by a chase fluid conduit 32 to allow chase fluid to flow from the chase fluid reservoir 18 into the first reservoir 12. A third valve 34 is disposed along the chase fluid conduit 32 between the chase fluid reservoir 18 and the first reservoir 12. The third valve 34 is capsable of being controlled by the processor 26 to adjust the flow of chase fluid from the chase fluid reservoir 18 to the first reservoir 12. The third valve 34 may be opened to allow fluid to flow from the chase fluid reservoir 18 to the first reservoir 12. In some embodiments, the third valve 34 may be adjusted to throttle the flow of fluid from the chase fluid reservoir 18 to the first reservoir 12.

The processor 26 can control the first valve 24, the second valve 30, and the third valve 34 independently or simultaneously. The processor 26 is configured to control fluid flow through the system 10. As shown, the processor 26 is in communication with the first valve 24 via a first lead 36, in communication with the second valve 30 via a second lead 38, and in communication with the third valve 34 via a third lead 40. The first lead 36, the second lead 38, and the third lead 40 each allows for a communication of a signal, such as by a conductor, an optical fiber, or wireless transmission.

In some embodiments, the first valve 24, the second valve 30, and the third valve 34 may be operated manually to override the processor 26.

In some embodiments, the processor 26 is a microprocessor. In some embodiments, the processor 26 is incorporated in a general purpose computer.

The system 10 may be configured for various specialized applications such as one or more of, but not limited to: sterile reception/storage of cells; automated mixing and delivery of reagents for protein expression, production, modification (e.g., post-translational modification) and/or secretion; automated monitoring protein expression, production, modification, and/or secretion; cell sorting and selection, including safe waste collection; cell washing and cell collection; cell seeding on or within a proliferation substrate or scaffold; automated mixing and delivery of proliferation reagents; proliferation of cells to expand cell populations; automated monitoring of cell conditions, including detection of confluence or growth phase; controlled cell release from the proliferation substrate or scaffold; repeated proliferation steps on selected surface area sizes to increase cell numbers; cell seeding on or within culture scaffold or matrix;

automatic monitoring of cell/tissue culture conditions; automatic monitoring of protein expression or secretion; mechanical and/or biochemical stimulation to promote proliferation; purification of the protein and/or recovery of the protein; and storage and transportation of cells and/or protein product.

According to an aspect of the present disclosure, a method of filtering a process fluid comprising a product is provided. In some embodiments, the product comprises an active pharmaceutical ingredient. The method can be performed by a system, such as the system 10 of FIG. 1. Some embodiments of the method include providing a system, such as the system of FIG. 1.

With reference to the system of FIG. 1, the method includes a first step of allowing some of the process fluid in the product holding tank (the first reservoir) 12 to flow out of the first reservoir 12 and pass the viral filter 14 to produce eluent. Upon reaching the end of fermentation in the first reservoir 12, the processor 26 causes the first valve 24 and the second valve 30 to open, allowing flow of cell culture fluid from the first reservoir 12 through the virus filter 14 to produce eluent. The eluent flows from the viral filter 14 into the eluent reservoir 16.

The method includes a second step of adding chase fluid from the chase fluid reservoir 18 to the process fluid in the first reservoir 12 to form a composite fluid in the first reservoir 12. In some embodiments, the amount of fluid in the first reservoir 12 is sensed by the sensor assembly 20 and, upon reaching a predetermined amount of fluid in the first reservoir 12, the processor 26 causes the third valve 34 to open, allowing flow of chase fluid from the chase fluid reservoir 18 into the first reservoir 12 to form the composite fluid in the first reservoir 12.

Upon reaching a preselected volume of composite fluid in the first reservoir 12, as signaled by the sensor assembly 20, the processor 26 causes third valve 34 to close, so that chase fluid is no longer added to the first reservoir 12 from the chase fluid reservoir 18.

In some embodiments, the second step of adding the chase fluid is performed prior to emptying of the first reservoir 12 of process fluid. When air enters the viral filter 14, the air in the viral filter 14 can stop flow through the system, which is undesirable. By keeping a sufficient amount of fluid in the first reservoir 12 before adding the chase fluid, the fluid level in the first reservoir is not at a low level that would allow air to enter the viral filter 14.

The volume of fluid in the first reservoir 12 just before the step of adding chase fluid can be selected such that air does not enter the viral filter 14. In some embodiments, the volume of fluid in the first reservoir 12 just before the step of adding chase fluid is related to the components that are downstream of the first reservoir 12, such as the combined volume of the viral filter 14, the pre-filter conduit 22, and the post filter conduit 28. In some embodiments, the volume of fluid in the first reservoir 12 just before the step of adding chase fluid is related to the components that are downstream of the first reservoir 14, such as the combined volume of the viral filter 14 and the pre-filter conduit 22.

In some embodiments, allowing some of the process fluid in the first reservoir 12 to flow out of the first reservoir 12 and through the viral filter 14 reduces an amount of process fluid remaining in the first reservoir 12.

In some embodiments, the second step of adding chase fluid to the first reservoir 12 is performed when the volume of process fluid remaining in the first reservoir 12 is at a reference volume or within a reference volume range. In some embodiments, the reference volume is equal to or greater than 0.5, 1, 1.5, 2, 3, 5 or 10, times the volume of the components disposed between the first reservoir 12 and a destination reservoir. For example, in some embodiments, the reference volume is equal to or greater than 0.5, 1, 1.5, 2, 3, 5 or 10, times the combined volume of the viral filter 14, the pre-filter conduit 22, and the post-filter conduit 28. In some embodiments, the reference volume is equal to or greater than the volume of the components disposed between the first reservoir 12 and a destination reservoir. For example, in some embodiments, the reference volume is equal to or greater than the combined volume of the viral filter 14, the pre-filter conduit 22, and the post-filter conduit 28.

In some embodiments, the volume of chase fluid added to the first reservoir 12 in the second step is at or less than or equal to a chase fluid reference volume. In some embodiments, the chase fluid reference volume is equal to or greater than 0.5, 1, 1.5, 2, 3, 5 or 10, times the volume of the components disposed between the first reservoir 12 and the destination reservoir. For example, in some embodiments, the chase fluid reference volume is equal to or greater than 0.5, 1, 1.5, 2, 3, 5 or 10, times the combined volume of the viral filter 14, the pre-filter conduit 22, and the post-filter conduit 28.

In some embodiments, the chase fluid reference volume is equal to or greater than the volume of the components disposed between the first reservoir and the destination reservoir. For example, in some embodiments, the chase fluid reference volume is equal to or greater than the combined volume of the viral filter 14, the pre-filter conduit 22, and the post-filter conduit 28.

In some embodiments, the chase fluid is added to the first reservoir 12 while the first reservoir 12 still contains a predetermined amount of process fluid. For example, in some embodiments, the chase fluid is added to the first reservoir 12 while the first reservoir 12 still contains at least 1, 2, 3, 4, 5, 10, 20, 30, 40, or 50% of the original amount of process fluid.

In some embodiments, the method includes operating the processor 26 to determine a value that is a function of the amount of process fluid remaining in the first reservoir 12. In some embodiments, the method includes operating the processor 26 to determine whether the value meets a predetermined reference value. In some embodiments if the value has a predetermined relationship with the reference value, chase fluid is added to the first reservoir 12.

In some embodiments, the predetermined relationship is that the value meets, exceeds, or is less than the reference value.

In some embodiments, the ratio of the amount of chase fluid to the amount of process fluid remaining in the first reservoir 12 when the chase fluid added is equal to or greater than 1:0.05, 1:1, 1.5:1, 2:1, 3:1, 5:1, or 10:1.

The method includes a third step of allowing the composite fluid, in the first reservoir 12 to flow out of the first reservoir 12 and pass the viral filter 14 to produce eluent.

In some embodiments, there is continuous flow from the first reservoir 12 to the viral filter 14 during one, two or all of the first step, the second step, and the third step of the method described above.

In some embodiments, flow of first reservoir fluid across the viral filter 14 is maintained in the absence of an interruption or slowing of flow of sufficient duration or magnitude that would be a significant impairment to viral removal. In some embodiments, flow is of sufficient duration or magnitude that a reduction in viral particles of at least 5, 10, 15, 20, 30, 40, 50, 60, 70, 80, 90, or 100 fold is achieved. In some embodiments, flow of first reservoir fluid across the viral filter 14 is maintained at a preselected rate.

In some embodiments, the chase fluid is added from the chase fluid reservoir 18 to the first reservoir 12 without stopping the flow of material from the first reservoir 12 through the viral filter 14 to the eluent reservoir 16 or another destination. By avoiding interruptions in the flow of product-containing fluid from the first reservoir 12 across the viral filter 14, a preparation of higher purity can be obtained. By maintaining flow from the first reservoir 12 to the viral filter 14 and from the viral filter 14 to the eluent reservoir 16, the purity or reduction of viral contamination of the eluent can be optimized. In some cases, if the flow from the first reservoir 12 to the eluent reservoir 16 stops, it may be necessary to reprocess a new process fluid.

In some embodiments, flow of a fluid from the first reservoir across the viral filter is maintained in the absence of an interruption or slowing of flow of duration or magnitude sufficient to substantially impair viral removal. In some embodiments, flow of fluid from the first reservoir across the viral filter is maintained in the absence of a stoppage of the flow.

In some embodiments, flow of fluid from the first reservoir across the viral filter is maintained in the absence of an interruption or slowing of flow of duration or magnitude sufficient to impair viral removal to a level below a log-reduction value of the viral filter. A typical viral filter has an associated log-reduction value that is reported or listed by the manufacturer. The log-reduction value varies based on the viral filter being used, and indicates the ability of a respective viral filter to remove viral content from a fluid as the fluid and viral content pass through the respective viral filter. If air enters the viral filter, the viral filtering process stops prematurely. If the viral filtering process stops prematurely, the results of the viral filtering step is invalidated.

In some embodiments, the method allows for continuous flow of fluid from the first reservoir 12 to the viral filter 14. In some embodiments, the flow of first reservoir fluid is stopped for a total of less than 1, 10, or 60 minutes. In some embodiments, any single stoppage of the flow of first reservoir fluid is less than 1, 10, or 60 minutes in duration. The method of the present disclosure allows for increased yield of product from the first reservoir.

Flow of first reservoir fluid across the viral filter is sufficient to avoid significant impairment to viral removal from the first reservoir 12, until a preselected event occurs. In some embodiments, the preselected event comprises eliminating a fluid connection between the viral filter and a second or destination reservoir. For example, the preselected event can comprise closing the second valve. In some embodiments, the preselected event comprises sending the eluent to a subsequent operation, such as the next unit operation. In some embodiments, the next unit operation includes liquid chromatography or ultrafiltration. In some embodiments, the preselected event comprises stopping the flow from the viral filter into the accumulated eluent. In some embodiments, the preselected event comprises stopping the flow from the viral filter into the second or destination reservoir. In some embodiments, the preselected event comprises collecting eluent produced from the flow of first reservoir fluid. In some embodiments, the preselected event is the collection of accumulated eluent. In some embodiments, the preselected event comprises reaching the end of a preselected time period.

In some embodiments, a preselected difference in pressure, such as a preselected range of differential pressure across the viral filter 14, is maintained. In some embodiments, the differential pressure across the viral filter 14 is maintained at or below a preselected maximal value. In some embodiments, the preselected differential pressure across the viral filter 14 that is maintained is equal to or no greater than 14 psi, 11 psi, or 13.2 psi. In some embodiments, the differential pressure across the viral filter 14 is maintained at or above a preselected minimal value. In some embodiments, the differential pressure across the viral filter 14 is sufficient that a reduction in viral particles of at least 5, 10, 15, 20, 30, 40, 50, 60, 70, 80, 90, or 100 fold is achieved. In some embodiments, the difference in pressure across the viral filter 14 can be measured by the difference between a first pressure sensed by a first pressure sensor at an inlet of the viral filter 14 and a second pressure sensed by a second pressure sensor at an outlet of the viral filter 14.

In some embodiments, when a preselected range of differential pressure across the viral filter 14 is maintained, the flow rate across the viral filter is in the range of one to 10 liters per minute. In some embodiments, when a preselected range of differential pressure across the viral filter 14 is maintained, the flow rate across the viral filter is 0.1, 0.2, 0.5, 1, 2, 4, 8, 10, 12, or 20 liters per minute.

Example Method

In one example method, upon reaching the end of fermentation, the processor 26 causes the first valve 24 and the second valve 30 to open, allowing flow of cell culture fluid from the first reservoir 12 through virus filter 14 and into the eluent reservoir 16. The sensor assembly 20 senses the amount of fluid in first reservoir 12. In some embodiments, the first reservoir 12 has a volume of 5,000 liters. Upon reaching a predetermined amount of fluid in the first reservoir 12, such as 200 kilograms of fluid, the processor 26 causes the third valve 34 to open, allowing flow of chase fluid from the chase fluid reservoir 18 into the first reservoir 12 to form composite fluid in the first reservoir 12. Upon reaching a preselected volume of composite fluid in the first reservoir 12, as signaled by sensor assembly 20, processor 26 causes the third valve 34 to close.

In some embodiments, the preselected volume of composite fluid in the first reservoir is 100 liters, 150 liters, 200 liters, 250 liters, or 300 liters. After further emptying of first reservoir 12, and upon reaching a preselected amount of composite fluid in first reservoir 12, sensor assembly 20 signals processor 26 which causes the second valve 30 to close. Processor 26 is configured to maintain a minimal level of flow from the first reservoir 12 through the virus filter 14 from the opening of the first valve 24 to drain the first reservoir 12 until eluent collection is completed. Processor 26 can be configured such that once flow through virus filter 14 reaches a minimal rate, e.g., stops, no eluent is allowed to flow into the eluent reservoir 16.

According to an aspect of the present disclosure, a method of filtering a process fluid comprising a product comprises a first step of allowing process fluid in a first reservoir to flow out of the first reservoir and to pass a viral filter to produce eluent and to reduce an amount of process fluid in the first reservoir. The method includes a second step of determining a value which is a function of the amount of process fluid remaining in the first reservoir and, if the value meets a predetermined reference value, adding chase fluid, to the process fluid in the first reservoir to form a composite fluid. In some embodiments, the chase fluid is added to the first reservoir while the first reservoir still contains a predetermined amount of process fluid. The method includes a third step of allowing the composite fluid in the first reservoir to flow out of the first reservoir and pass the viral filter to produce eluent. The method includes a fourth step of stopping the flow from the viral filter into the accumulated eluent. In some embodiments, flow of first reservoir fluid across the viral filter is sufficient to avoid significant impairment to viral removal or removal of the first reservoir fluid, until stopping the flow from the viral filter into the accumulated eluent.

Viral Filters

Various filtration approaches can be used to remove virus particles from culture or other fluid containing products for use in medical and veterinary applications. Size exclusion filtration has many advantages. Typically it does not alter the structural or functional properties of polypeptide products and provides non-specific removal of viruses.

Hollow fiber membrane filters are particularly well suited to removal of viral particles. Hollow fiber membrane filters include bundles of parallel hollow fibers configure roughly as a bundle of straws. The wall of each hollow fiber has a three-dimensional web structure of pores comprised of voids interconnected by fine capillaries. While not wishing to be bound by theory, it is believed that through a size exclusion mechanism, the membrane allows proteins to easily pass through the hollow fiber walls while viruses are retained. During filtration of protein solutions, viruses are removed and proteins permeate the membrane. The method can provide high protein recovery rates without adsorption or denaturation.

Exemplary hollow fiber filters include hydrophilic modified polyvinylidene fluoride (PVDF) hollow fiber membranes. The filter element can be disposed in an inert cartridge configured at each end for insertion into a production line. Exemplary virus filters include Planova™ 15N, 20N, 35N and 75N filters, Planova™ BioEX filters as well as filters that are substantially similar to these filters.

In an embodiment, methods described herein provide product solutions having a viral reduction (after filter passage) of at least 5, 10, 15, 20, 30, 40, 50, or 100 fold.

In some embodiments, methods described herein provide a log-reduction value of ~12-18 $\log_{10}$ clearance for endogenous retroviruses and ~6 $\log_{10}$ removal for adventitious viruses.

Other filters which can be used in the methods described herein include, e.g., tangential flow filters.

Reactors

The methods of optimizing viral removal disclosed herein can be used with a bioreactor, or, more generally with any feed source. Typically, a bioreactor is not immediately upstream from the filter but rather the feed to the filter is from a vessel, e.g., a product holding tank, downstream from the bioreactor. The devices, facilities, and methods can include any suitable reactor(s) including but not limited to stirred tank, airlift, fiber, microfiber, hollow fiber, ceramic matrix, fluidized bed, fixed bed, and/or spouted bed bioreactors. The reactors can be connected directly with a viral filter or can have other elements, e.g., other vessels, such as holding tanks, disposed between the reactor and the viral filter. As used herein, "reactor" can include a fermenter or fermentation unit, or any other reaction vessel or suitable reservoir and the term "reactor" is used interchangeably with "fermenter."

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, YO, C127, L cell, COS, e.g., COS1 and COS7, QC1-3,HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57BI/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii,*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina,* or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or other prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto,* or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleukin, denileukin diftitox, interferon alpha-n3 (injection), interferon alpha-nl, DL-8234, interferon, Suntory (gamma-la), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Derp1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE 1

| Protein Product | Reference Listed Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |

TABLE 1-continued

| Protein Product | Reference Listed Drug |
|---|---|
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |

TABLE 1-continued

| Protein Product | Reference Listed Drug |
|---|---|
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
|  | Darbepoetin-α | Aranesp |
|  | Growth hormone (GH), somatotropin | Genotropin, Humatrope, Norditropin, NovIVitropin, Nutropin, Omnitrope, Protropin, Siazen, Serostim, Valtropin |
|  | Human follicle-stimulating hormone (FSH) | Gonal-F, Follistim |
|  | Human chorionic gonadotropin | Ovidrel |
|  | Lutropin-α | Luveris |
|  | Glucagon | GlcaGen |
|  | Growth hormone releasing hormone (GHRH) | Geref |
|  | Secretin | ChiRhoStim (human peptide), SecreFlo (porcine peptide) |
|  | Thyroid stimulating hormone (TSH), thyrotropin | Thyrogen |
| Blood Clotting/Coagulation Factors | Factor VIIa | NovoSeven |
|  | Factor VIII | Bioclate, Helixate, Kogenate, Recombinate, ReFacto |
|  | Factor IX | Benefix |
|  | Antithrombin III (AT-III) | Thrombate III |
|  | Protein C concentrate | Ceprotin |
| Cytokine/Growth factor | Type I alpha-interferon | Infergen |
|  | Interferon-αn3 (IFNαn3) | Alferon N |
|  | Interferon-β1a (rIFN-β) | Avonex, Rebif |
|  | Interferon-β1b (rIFN-β) | Betaseron |
|  | Interferon-γ1b (IFN γ) | Actimmune |
|  | Aldesleukin (interleukin 2(IL2), epidermal theymocyte activating factor; ETAF | Proleukin |
|  | Palifermin (keratinocyte growth factor; KGF) | Kepivance |
|  | Becaplemin (platelet-derived growth factor; PDGF) | Regranex |
|  | Anakinra (recombinant IL1 antagonist) | Anril, Kineret |
| Antibody molecules | Bevacizumab (VEGFA mAb) | Avastin |
|  | Cetuximab (EGFR mAb) | Erbitux |
|  | Panitumumab (EGFR mAb) | Vectibix |

TABLE 2-continued

Exemplary Products

| Therapeutic Product type | Product | Trade Name |
|---|---|---|
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A method of filtering a process fluid comprising a pharmaceutical product, the method comprising:
   a) allowing some of the process fluid in a first reservoir to flow out of the first reservoir, reducing an amount of process fluid remaining in the first reservoir, and pass a size exclusion viral filter to produce a first eluent;
   b) adding a chase fluid from a chase fluid reservoir to the process fluid in the first reservoir to form a composite fluid, and wherein a ratio of an amount of chase fluid to an amount of process fluid remaining in the first reservoir when the chase fluid is added is equal to or greater than 1:1; and
   c) allowing the composite fluid in the first reservoir to flow out of the first reservoir and pass the size exclusion viral filter to produce a second eluent,
   wherein the composite fluid does not include the first or second eluent,
   wherein the flow of the process fluid or the composite fluid across the size exclusion viral filter is continuous such that air does not enter the size exclusion viral filter until a preselected event occurs.

2. The method of claim 1, wherein the pharmaceutical product includes an active pharmaceutical ingredient.

3. The method of claim 1, wherein adding the chase fluid is performed when the volume of process fluid remaining in the first reservoir is at a reference volume or within a reference volume range.

4. The method of claim 3, wherein the reference volume is equal to or greater than 0.5 times a volume of components disposed between the first reservoir and a destination reservoir, wherein the volume of components comprises the combined volume of the size exclusion viral filter, a pre-filter conduit, and a post filter conduit.

5. The method of claim 3, wherein the reference volume is equal to or greater than a volume of components disposed between the first reservoir and a destination reservoir, wherein the volume of components comprises the combined volume of the size exclusion viral filter, a pre-filter conduit, and a post filter conduit.

6. The method of claim 1, wherein the volume of chase fluid added is less than or equal to a chase fluid reference volume, wherein the chase fluid reference volume is equal to or greater than 0.5 times a volume of components disposed between the first reservoir and a destination reservoir, and wherein the volume of components comprises the combined volume of the size exclusion viral filter, a pre-filter conduit, and a post filter conduit.

7. The method of claim 6, wherein the chase fluid reference volume is equal to or greater than a volume of components disposed between the first reservoir and the destination reservoir, wherein the volume of components comprises the combined volume of the size exclusion viral filter, a pre-filter conduit, and a post filter conduit.

8. The method of claim 1, wherein the chase fluid is added to the first reservoir while the first reservoir still contains a predetermined amount of process fluid.

9. The method of claim 1, wherein a ratio of an amount of chase fluid to an amount of process fluid remaining in the first reservoir when the chase fluid is added is equal to or greater than 1.5:1.

10. The method of claim 1, wherein a preselected difference in pressure across the size exclusion viral filter is maintained.

11. The method of claim 1, wherein a differential pressure across the size exclusion viral filter is maintained at or below a preselected maximal value.

12. The method of claim 1, wherein a preselected difference in pressure, equal to or no greater than 14 psi of differential pressure across the size exclusion viral filter is maintained.

13. The method of claim 1, wherein a differential pressure across the size exclusion viral filter is maintained at or above a preselected minimal value.

14. The method of claim 1, wherein a differential pressure across the size exclusion viral filter sufficient that a reduction in viral particles of at least 5 fold is achieved.

15. The method of claim 1, wherein the preselected event includes reaching the end of a preselected time period.

16. The method of claim 1, further comprising:
providing a system including
the first reservoir,
the size exclusion viral filter, and
a destination reservoir,
wherein the first reservoir is in fluid connection with the size exclusion viral filter and the size exclusion viral filter is in fluid connection with the destination reservoir.

17. The method of claim 16, wherein the size exclusion viral filter is disposed between the first reservoir and the destination reservoir.

18. The method of claim 16, wherein the size exclusion viral filter is disposed between the first reservoir and a conduit.

19. The method of claim 16, wherein the system includes a pre-filter conduit configured to convey the process fluid or the composite fluid from the first reservoir to the size exclusion viral filter.

20. The method of claim 16, wherein the system includes a conduit configured to convey the process fluid or the composite fluid to the destination reservoir or a conduit to a destination.

21. The method of claim 16, wherein the system includes
a first conduit configured to convey the process fluid or the composite fluid from the first reservoir to the size exclusion viral filter, and
a second conduit configured to convey the first or the second eluent from the size exclusion viral filter to the destination reservoir.

22. The method of claim 16, wherein the system includes a first valve disposed to control the flow of the process fluid or the composite fluid from the first reservoir to the size exclusion viral filter.

23. The method of claim 16, wherein the system includes a valve disposed to control the flow of the first or the second eluent from the size exclusion viral filter to the destination reservoir.

24. The method of claim 1, wherein flow of the process fluid or the composite fluid from the first reservoir across the size exclusion viral filter is maintained in the absence of a stoppage of the process fluid or the composite fluid flow.

25. A method of filtering a process fluid comprising a pharmaceutical product, comprising:
a) allowing process fluid in a first reservoir to flow out of the first reservoir and pass a size exclusion viral filter to produce a eluent first and to reduce an amount of process fluid in the first reservoir;
b) determining a value which is a function of the amount of process fluid remaining in the first reservoir and, if the value meets a predetermined reference value, adding chase fluid from a chase fluid reservoir, to the process fluid in the first reservoir to form a composite fluid, wherein the chase fluid is added to the first reservoir while the first reservoir still contains a predetermined amount of process fluid, and wherein a ratio of an amount of chase fluid to an amount of process fluid remaining in the first reservoir when the chase fluid is added is equal to or greater than 1:1;
c) allowing the composite fluid in the first reservoir to flow out of the first reservoir and pass the viral filter to produce a second eluent; and
d) stopping the flow from the size exclusion viral filter, wherein the composite fluid does not include the first or second eluent,
wherein the flow of the process fluid or the composite fluid from the first reservoir across the viral filter is continuous such that air does not enter the size exclusion viral filter until stopping the flow from the size exclusion viral filter.

26. The method of claim 1, wherein the chase fluid is added to the first reservoir at a first flow rate which matches a second flow rate of process fluid or composite fluid from the first reservoir to the size exclusion viral filter.

27. The method of claim 1, wherein the size exclusion viral filter is a hollow fiber membrane filter.

* * * * *